United States Patent [19]

Keefer et al.

[11] Patent Number: 5,208,233
[45] Date of Patent: May 4, 1993

[54] ANTI-HYPERTENSIVE COMPOSITIONS OF SECONDARY AMINE-NITRIC OXIDE ADDUCTS AND USE THEREOF

[75] Inventors: Larry K. Keefer, Bethesda; David A. Wink, Hagerstown, both of Md.; Tambra M. Dunams, Florence, Ala.; Joseph A. Hrabie, Frederick, Md.

[73] Assignee: The United States of America as represented by the Department of Health and Human Services, Washington, D.C.

[21] Appl. No.: 743,892

[22] Filed: Aug. 12, 1991

Related U.S. Application Data

[63] Continuation-in-part of Ser. No. 409,552, Sep. 15, 1989, Pat. No. 5,039,705.

[51] Int. Cl.$^5$ .................... A61K 31/33; A61K 31/535
[52] U.S. Cl. .................... 514/231.8; 514/183; 514/231.2; 514/238.8
[58] Field of Search .............. 514/231.2, 238.8, 231.8, 514/183

[56] References Cited

U.S. PATENT DOCUMENTS

| | | | |
|---|---|---|---|
| 3,153,094 | 10/1964 | Reilly | 260/576 |
| 3,950,332 | 4/1976 | Anderson | 260/247.2 A |
| 4,954,526 | 9/1990 | Keefer | 514/611 |
| 5,039,705 | 8/1991 | Keefer et al. | 514/611 |

FOREIGN PATENT DOCUMENTS 1348165 3/1974 United Kingdom .

OTHER PUBLICATIONS

Nature, vol. 345, pp. 161–162, (1990).
L. J. Ignarro, The FASEB Journal, vol. 3, Jan. 1989, pp. 31–36.
Palmer et al, Nature, vol. 327, Jun. 1987, pp. 524–526.
F. V. DeFeudis, Drugs of Today, vol. 24, No. 2 (1988), pp. 103–115.
T. J. Hansen et al, IARC Sci. Publ., pp. 21–29.
Kruszyna et al, Tox. & Appl. Pharmacol., vol. 91, pp. 429–438 (1987).
L. J. Ignarro et al, J. Pharmacol. Exper. Therapeutics; vol. 218, No. 3, pp. 739–749 (1981).
"Free Radicals in Inorganic Chemistry", No. 36, Am. Chem. Soc. pp. 143–149 (1962).
Drago et al, J. Am. Chem. Soc., vol. 83 pp. 1819–1822 (1961).
"Pharmaceutics & Pharmacy Practice", J. B. Lippincott Col, Philadelphia (1982) edited by Bander & Chalmers, pp. 238–250.
ASHP Handbook on Injectable Drugs, 4th Edition, by Trissel pp. 622–630.
F. Murad et al, Propr. Clin. Biol. Res., No. 249, pp. 65–76 (1987).
R. M. Rapoport et al, Protein Phosph. Research S(4–5), pp. 281–296 (1983).
R. F. Furchgott, Ann. Rev. Pharmacol. Toxicol., vol. 24, pp. 175–197 (1984).

*Primary Examiner*—Allen J. Robinson
*Attorney, Agent, or Firm*—Birch, Stewart, Kolasch & Birch

[57] ABSTRACT

There are disclosed anti-hypertensive compositions and a method of lowering blood pressure in mammals. The active component in the anti-hypertensive compositions is a compound of the formula

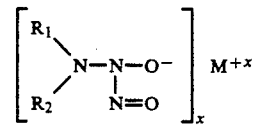

wherein $R_1$ and $R_2$ are independently selected from straight chain and branched chain $C_1$–$C_{12}$ alkyl groups and benzyl, with the proviso that no branch occur on the alpha carbon atom of the alkyl group; or $R_1$ and $R_2$ together with the nitrogen atom they are bonded to form a heterocyclic ring; $M^{+x}$ is a pharmaceutically acceptable cation, wherein x is the valence of the cation.

8 Claims, 2 Drawing Sheets

ANTI-HYPERTENSIVE COMPOSITIONS OF SECONDARY AMINE-NITRIC OXIDE ADDUCTS AND USE THEREOF

The present application is a continuation-in-part application of U.S. patent application Ser. No. 07/409,552, filed on Sep 15, 1989, now U.S. Pat. No. 5,039,705, which is expressly incorporated by reference herein, in its entirety.

FIELD OF THE INVENTION

The present invention relates to novel pharmaceutical compositions and to a method of treating hypertension. Related compositions and methods are described in U.S. Pat. No. 4,954,526, issued Sep. 4, 1990 and U.S. patent application Ser. No. 07/423,279, filed on Oct. 18, 1989 and in U.S. patent application Ser. No. 07/585,793, filed on Sep. 20, 1990, U.S. Pat. No. 5,155,137, each of which is incorporated herein by reference in its entirety.

BACKGROUND OF THE INVENTION

Endothelium-derived relaxing factor (EDRF) is a labile humoral agent which is part of a cascade of interacting agents involved in the relaxation of vascular smooth muscle. EDRF is thus important in the control of vascular resistance to blood flow and in the control of blood pressure. Some vasodilators act by causing EDRF to be released from endothelial cells. (See Furchgott, Ann. Rev. Pharmacol. Toxicol. 24, 175–197, 1984.) Recently, Palmer et al., have shown that EDRF is identical to the simple molecule, nitric oxide, NO (Nature 317, 524–526, 1987). It has been hypothesized for years that many nitrovasodilators that mimic the effect of EDRF, like glyceryl trinitrate, amyl nitrite, $NaNO_2$ and sodium nitroprusside (SNP), do so by virtue of their conversion to a common moiety, namely NO, which is also a vasodilator. (See Kruszyna et al., Tox.& Appl. Pharmacol.,91, 429–438, 1987; Ignarro, FASEB J. 3, 31–36, 1989 and Ignarro et al., J. Pharmacol. Exper. Theraputics 218(3), 739–749, 1981.)

SUMMARY OF THE INVENTION

It has now been discovered that certain compounds encompassed by the structure:

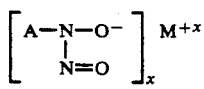

wherein A is a secondary amino group, $M^{+x}$ is a pharmaceutically acceptable cation and x is the valence of the cation, are potent anti-hypertensives and thus are useful for treating cardiovascular disorders in which lowering the blood pressure has a beneficial result. It is believed that these compounds function by releasing NO in the blood after injection; however the invention should not be limited by this hypothesis. These compounds are for the most part known. However, there is no suggestion in the previous literature that they are anti-hypertensive, indeed, there is no suggestion in the previous art that these compounds have any pharmaceutical use. Nonetheless, some of the compounds are described by Drago in "Free Radicals in Inorganic Chemistry", Number 36, Advances in Chemistry Series, American Chemical Society, Wash. D.C., 1962, pages 143–149 and by Drago et al, J. Amer. Chem. Soc. 83, 1819–1822, 1961. These two articles by Drago are incorporated herein by reference, in their entirety. The two Drago references mention no utility for the compounds whatsoever. Similarly, Reilly, in U.S. Pat. No. 3,153,094, also discloses some of these compounds at columns 11-13 thereof, but does not teach any biological activity thereof.

BRIEF DESCRIPTION OF THE DRAWINGS

The present invention will become more fully understood from the detailed description given here and below and the accompanying drawings which are given by way of illustration only, and thus, are not limitative of the present invention, and wherein.

Figure 1:
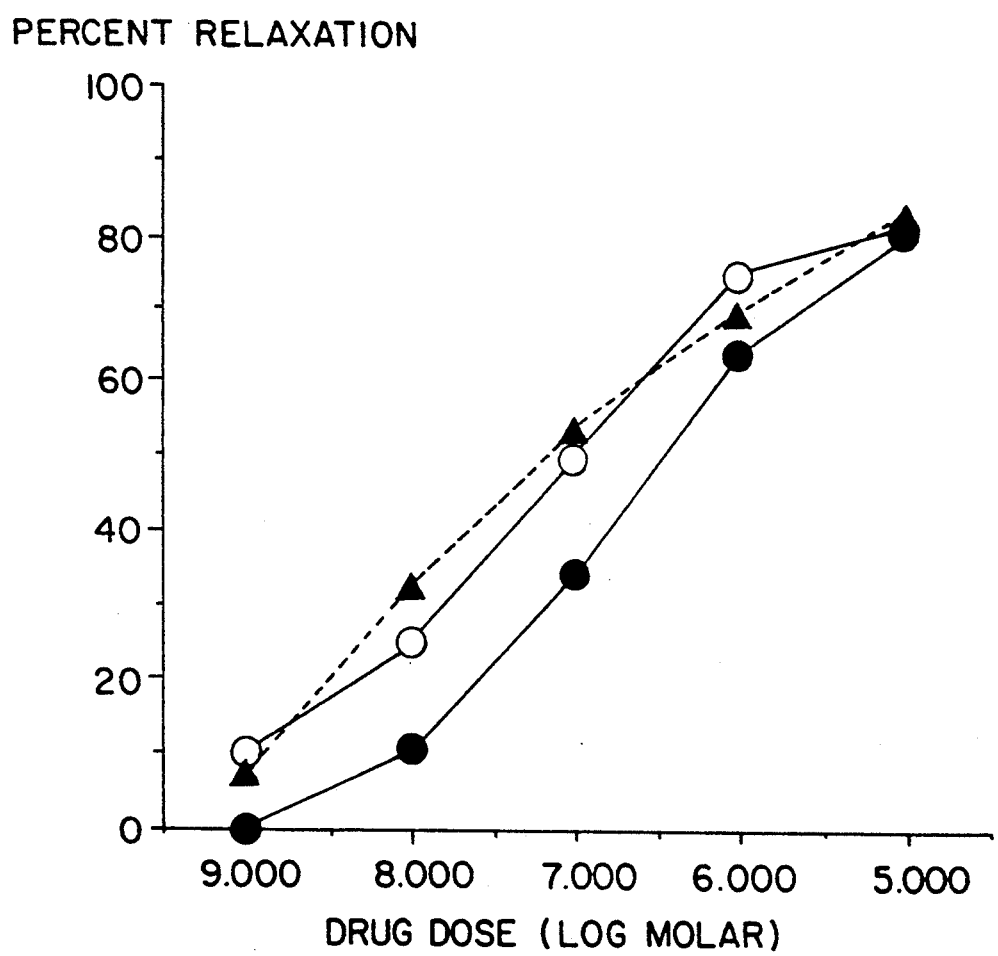
FIG. 1

Dose response curve obtained in Pharmacology Experiment II, below, wherein the bis(piperidino)bis(nitric oxide) Adduct of Example 2 was tested for vasorelaxant activity by utilizing a standard isolated vascular ring preparation:

▲ = Bis(piperidino)bis(nitric oxide) Adduct of Example 2 (mean);

○ = glyceryl trinitrate (mean)

● = sodium nitroprusside (mean).

FIG. 2

Dose response curve obtained in Pharmacology Experiment II, below, wherein the bis(morpholino)bis(nitric oxide) Adduct of Example 3 was tested for vasorelaxant activity by utilizing a standard isolated vascular ring preparation:

△ = Bis(morpholino)bis(nitric oxide) adduct of Example 3 (mean);

○ = glyceryl trinitrate (mean);

● = sodium nitroprusside (mean).

DETAILED DESCRIPTION OF THE INVENTION

The present invention provides pharmaceutical compositions comprising: a compound of the following formula I

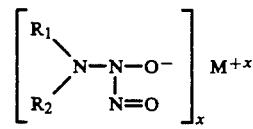

wherein $R_1$ and $R_2$ are independently selected from straight chain and branched chain alkyl groups of one to twelve carbon atoms or benzyl, with the proviso that no branch occur on the alpha carbon of the alkyl groups, or $R_1$ and $R_2$ together with the nitrogen atom they are bonded to form a heterocyclic group, preferably selected from the group consisting of

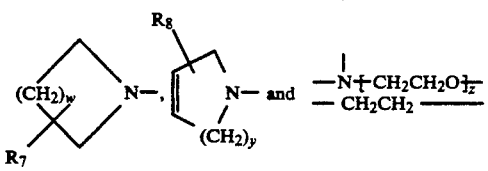

wherein w is 1 to 12, y is 1 or 2, z is 1 to 5, $R_7$ is hydrogen, $C_{1-8}$ straight chain alkyl, $C_{3-6}$ branched chain alkyl, $C_{3-8}$ cycloalkyl, phenyl or tolyl, and $R_8$ is hydrogen $C_{1-6}$ straight chain alkyl or $C_{3-6}$ branched chain alkyl; $M^{+x}$ is a pharmaceutically acceptable cation, wherein x is the valence of the cation (its charge); and a pharmaceutically acceptable carrier. By straight chain alkyl is meant the non-branched methyl, ethyl, n-propyl, n-butyl, n-decyl, and like groups. By branched chain alkyl is meant groups like 3-methylpentyl, 2-methylpropyl, and the like. The proviso means that groups like isopropyl or 1-methylbutyl are excluded. The $C_1$ to $C_6$ alkyls are preferred. Of the $R_1R_2N$- heterocyclic groups encompassed thereby, there are mentioned, for example, azetidino, pyrrolidino, piperidino, azacylooctane, substituted piperidino (e.g. 2-methyl, 3-methyl, 4-methyl, 2-ethyl, 4-phenyl, 2-propyl, 4-propyl and 4-tert.butyl-piperidino), substituted pyrrolidino (e.g., 2-methyl and 3-methylpyrrolidino), 1,2,3,6-tetrahydropyridino, 3-pyrrolino, morpholino, hexamethyleneimino, 1-aza-12-crown-4, 1-aza-15-crown-5 and 1-aza-18-crown-6. Morpholino is a preferred $R_1R_2N$- moiety. Many commercially available nitrogen-containing heterocyclic compounds can be used to prepare compounds of Formula I wherein $R_1R_2N$- is a heterocyclic moiety. For example, such compounds can be obtained from the chemical companies of Aldrich; American Tokyo Kasei, Inc.; Reilly Industries, Inc.; and Pfaltz and Bauer.

By a pharmaceutically acceptable cation is meant any non-toxic cation; these are well known to one of ordinary skill in the art. The cation should not render the compound unstable or insoluble in water. Generally the cation will be a group 1 or group 2 cation, such as sodium, potassium, magnesium or calcium ions, or $NR_3R_4R_5R_6^+$, wherein $R_3$, $R_4$, $R_5$, and $R_6$ are independently chosen from H, $C_1$-$C_{12}$ alkyl, $C_3$-$C_7$ cycloalkyl or benzyl, more preferably H, $C_1$-$C_4$ alkyl or $C_6$ cycloalkyl. The method of synthesis discussed below first results in the cation being $R_1R_2H_2N^+$, these cations work well. The most preferred cations are $Na^+$, $K^+$, $Ca^{+2}$, and $R_1R_2H_2N^+$.

The compositions are potent anti-hypertensives. They are useful for lowering the blood pressure and treating any cardiovascular disorder in which lowering the blood pressure will have a beneficial effect. The invention provides an effective method of lowering the blood pressure by administering the composition to a mammal.

The methods of synthesis are the same as disclosed by Drago et al., J. Amer. Chem. Soc., 83, 1819-1822, 1961. Generally, the secondary amine ($R_1R_2HN$) is dissolved in anhydrous ether, oxygen is removed from the system, the temperature is lowered to $-78°$ C., and dry NO is bubbled through the ether solution. The reaction can be run at high pressure (100 psi) or at atmospheric pressure. The same product is obtained, but the yields are higher using the high pressure method. The same methodology is used to make all the compounds, with the only principal difference being the starting secondary amine. Examples 1a and 1b give the details of how the diethylamine complex was made, while Examples 2-4 describe the preparation of secondary heterocyclic amine-nitric oxide complexes.

EXAMPLE 1a

Preparation of Bis(diethylamino)bis(nitric oxide) Adduct

Anhydrous diethylamine (100 ml) was dissolved in 100 ml of anhydrous diethyl ether and was placed in a three-necked flask. Two of the necks served as inlets for $N_2$ and NO, and the third was an outlet. The flask was flushed with $N_2$ and the mixture cooled to $-78°$ C. using an acetone-dry ice bath. Commercial grade NO was bubbled through 10M NaOH and dried by passing it through a column containing NaOH pellets, and then bubbled for 3 hr through the diethylamine/diethyl ether solution. The mixture was allowed to warm to room temperature overnight (18 hr). The product precipitated from solution. The product was filtered and washed with diethyl ether. Three grams (3% yield) of crude product was obtained. The product was purified by suspending it in diethyl ether, adding sufficient neutralized chloroform dropwise to just dissolve the product, and placing the mixture in the freezer. The resultant crystals were then filtered, washed with diethyl ether and dried by vacuum.

$^1$H NMR (200 MHz): 3.07(q, 4H, J=7.2 Hz), 2.94(q, 4H, J=7.2Hz), 1.27(t, 6H, J=7.2Hz), 0.96(t, 6H, J=7.2 Hz).

—C NMR (50 MHz): 51.3, 45.2, 13.8, 13.5. Calculated: C=46.56%, N=27.17%, H=10.75%. Found: C=46.49%, N=26.29, H=11.20%.

The above physico-chemical characteristics correspond to the structure:

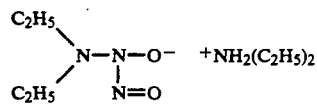

EXAMPLE 1b

Preparation of Bis(diethylamino)bis(nitric oxide) Adduct

In the high pressure method a Parr shaker was used. NO was added to the reservoir which makes it possible to fill the reaction vessel without opening it directly to the NO tank. The mixture of diethylamine (100 ml) and diethyl ether (100 ml) was added to the reaction vessel. The reaction vessel was cooled to $-78°$ C. and subjected to several evacuation/nitrogen flush cycles to remove as much of the oxygen as possible. NO was then introduced at a pressure of about 100 psi. The reaction vessel was allowed to slowly warm to room temperature overnight (18 hr), with shaking. The excess NO was flushed off with $N_2$ and the product was filtered and washed with diethyl ether. The crude yield was 5 grams. Purification and analysis were the same as in Example 1a.

EXAMPLE 2

Preparation of Bis(piperidine)bis(nitric oxide) Adduct

To conduct this preparation, the Parr apparatus was modified by remounting the bottle clamp such that stirring with a magnetic stirrer was possible. Yields are thus greatly improved.

A solution of 50.0 ml piperidine (0.506 mol) in 150 ml ether was deoxygenated for 5 minutes with nitrogen and placed in the Parr holder. The solution was stirred vigorously, cooled in a large dry ice bath and NO admitted to a pressure of 75 psig. Both dry ice and NO were replenished for the next 4 hours and then the reaction was left to slowly approach room temperature overnight. After 16 hours, the NO pressure at room temperature was 70 psig and this was vented. The slurry was flushed with nitrogen and filtered. The white solid was washed with ether and dried in vacuo for 3 hours to afford 42.7 g of crystalline colorless product, m.p. 78°-79° C. dec., yield 73%. $^1$H NMR ($D_2O$) 1.4-1.6 (m, 2H), 1.6–1.8 m, 10H , 3.06 (t, 4H, J=5.6 Hz), 3.15 (t, 4H, J=5.5 Hz). $^{13}$C NMR (D$_2$O) 24.50, 25.23 (2C), 25.36, 27.44 (2C), 47.41 (2C), 55.84 (2C).

The above physico-chemical characteristics correspond to the structure

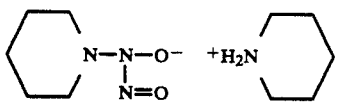

EXAMPLE 3

Preparation of Bis(morpholino)bis(nitric oxide) Adduct

This material was prepared utilizing the methodology herein disclosed to prepare other compounds encompassed by the present invention (e.g., Example 2) by reacting morpholine with nitric oxide. The prepared compound exhibited the following $^1$H NMR spectrum: 2.7–2.9 (m, 4H), 3.1–3.2 (m, 4H), 3.6–3.8 (m, 4H), 3.9–4.0 (m, 4H); and ultraviolet spectrum: $\lambda_{max}$ ($\epsilon$) 252 nm (8.8×10$^3$ M$^{-1}$ cm$^{-1}$).

The above physico-chemical characteristics correspond to the structure:

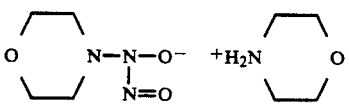

EXAMPLE 4

Preparation of Bis(pyrrolidino)bis(nitric oxide) Adduct

The title compound is prepared by substituting pyrrolidine for piperidine in the preparation recited in Example 2. The compound of Formula I which is produced possesses the following formula:

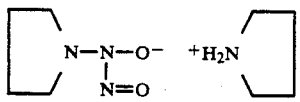

EXAMPLE 5

Utilizing the procedure set forth in Example 2, and substituting the following nitrogen-containing heterocyclics for piperidine:

(a) azetidine,
(b) azacylooctane,
(c) 2-methylpiperidine,
(d) 3-methylpiperidine,
(e) 4-methylpiperidine,
(f) 2-ethylpiperidine,
(g) 4-phenylpiperidine,
(h) 2-propylpiperidine,
(i) 4-propylpiperidine,
(j) 4-tert.butylpiperidine,
(k) 2-methylpyrrolidine,
(l) 3-methylpyrrolidine,
(m) 1,2,3,6-tetrahydropyridine,
(n) 3-pyrroline,
(o) hexamethyleneimine,
(p) 1-aza-12-crown-4,
(q) 1-aza-15-crown-5, and
(r) 1-aza-18-crown-6 there are obtained the following Formula I compounds:

(a) bis (azetidine) bis (nitric oxide) adduct,
(b) bis (azacylooctane) bis (nitric oxide) adduct,
(c) bis (2-methylpiperidine) bis (nitric oxide) adduct,
(d) bis (3-methylpiperidine) bis (nitric oxide) adduct,
(e) bis (4-methylpiperidine) bis (nitric oxide) adduct,
(f) bis (2-ethylpiperidine) bis (nitric oxide) adduct,
(g) bis (4-phenylpiperidine) bis (nitric oxide) adduct,
(h) bis (2-propylpiperidine) bis (nitric oxide) adduct,
(i) bis (4-propylpiperidine) bis (nitric oxide) adduct,
(j) bis (4-tert.butylpiperidine) bis (nitric oxide) adduct,
(k) bis (2-methylpyrrolidine) bis (nitric oxide) adduct,
(l) bis (3-methylpyrrolidine) bis (nitric oxide) adduct,
(m) bis (1,2,3,6-tetrahydropyridine) bis (nitric oxide) adduct,
(n) bis (3-pyrroline) bis (nitric oxide) adduct,
(o) bis (hexamethyleneimine) bis (nitric oxide) adduct,
(p) bis (1-aza-12-crown-4) bis (nitric oxide) adduct,
(q) bis (1-aza-15-crown-5) bis (nitric oxide) adduct, and
(r) bis (1-aza-18-crown-6) bis (nitric oxide) adduct.

The other secondary amine-NO complexes encompassed hereby are made using the same methods as used in Examples 1a to 5, the only principal difference being the identity of the starting secondary amines. The product made in each case has the formula $R_1R_2NN_2O_2^- R_1R_2H_2N^+$. The synthesis of the salts containing the other cations is done by conventional methods, most particularly by a metathesis reaction, a method well known to one of ordinary skill in the art. (See Drago et al.) To make the sodium salt of the compound produced in example 1, the diethylammonium salt is dissolved in ethyl alcohol and reacted with sodium ethoxide according to the following reaction:

$R_1R_2NN_2O_2^- R_1R_2H_2N^+ + NaOEt \rightarrow EtOH + R_1$-$R_2NH + R_1R_2NN_2O_2^- Na^+$.

The product is precipitated by flooding the reaction mixture with ether and then washed with neutralized chloroform. The other salts can be made by similar metathesis reactions.

PHARMACOLOGICAL PROPERTIES

Pharmacology Experiment I

The effect on the mean arterial blood pressure and heart rate of male Sprague-Dawley rats of a composition of the present invention containing the compound of Example 1 was measured using a standard technique. A pressure transducer (Bell and Howell, type 4-327-I) was connected to the right carotid artery via a catheter containing heparinized saline. The mean arterial pressure and heart rate were recorded on a Gould (Model 2800) 8-channel recorder. The rats were anesthetized with nembutal at a initial dose of 35 mg/kg body weight and recurrent smaller injections as needed. The compounds were dissolved in a pharmaceutical carrier and injected into the rats via a catheter in the right femoral vein. Table 1 shows the results obtained.

TABLE 1

| Compound | Dose (μmole/kg) | Mean Arterial Pressure (mm Hg) | | | Heart Rate (beats/min) | |
|---|---|---|---|---|---|---|
| | | Initial | Post | Change | Initial | Post |
| (Et)$_2$NN$_2$O$_2^-$ | 3.90 | 102 | 36 | −66 | 480 | 480 |

TABLE 1-continued

| Compound | Dose (μmole/kg) | Mean Arterial Pressure Initial (mm Hg) | Mean Arterial Pressure Post (mm Hg) | Mean Arterial Pressure Change (mm Hg) | Heart Rate Initial (beats/min) | Heart Rate Post (beats/min) |
|---|---|---|---|---|---|---|
| $(Et)_2H_2^+$ SNP | 0.34 | 113 | 56 | −57 | 403 | 454 |
| $NaNO_2$ | 4.00 | 126 | 48 | −78 | 360 | 420 |
| $NaNO_3$ | 42.00 | 117 | 120 | 3 | 420 | 420 |

In Table 1, the pharmaceutical carrier was Abbott's 5% dextrose USP. SNP, $NaNO_2$, and $NaNO_3$ were used as controls. SNP and $NaNO_2$ are known vasodilators, $NaNO_3$ is the oxidative breakdown product of $NaNO_2$ and has little vasodilatory effect. The results show that $(Et)_2NN_2O_2^- \cdot (Et)_2H_2N^+$ is a potent anti-hypertensive, decreasing the blood pressure significantly. The peak value of the blood pressure decrease, shown in Table 1, takes only about 30 seconds to 1 minute to occur, after injection, and the blood pressure starts to rise again soon after and has totally recovered within 10 to 15 minutes.

Pharmacology Experiment II

The vasorelaxant activities of secondary heterocyclic amine-nitric oxide complexes was tested.

Figure 2:
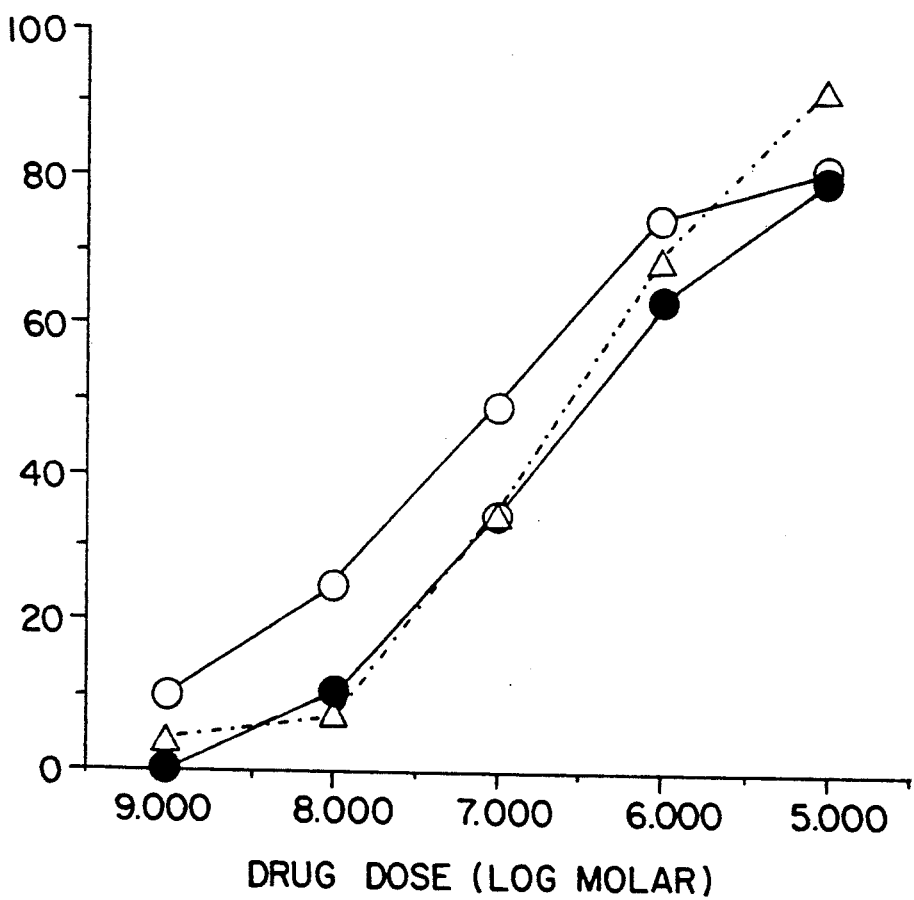

A standard isolated vascular ring preparation was used to establish the potencies of the compounds of Examples 2 and 3, described above. In the test procedures utilized, thoracic aortic rings from New Zealand White rabbits were suspended in pH 7.4 buffer at 37° C. and a 10 g preload was applied to each. After equilibration for 2 hours, the rings were preconstricted with norepinephrine. By measuring the grams of relaxation induced by adding the complexes to the organ baths at successively increasing concentrations from $10^{-9}$ to $10^{-5}$ M, a dose-response curve was constructed for each compound as shown in FIGS. 1 and 2. The piperidine derivative (Example 2, FIG. 1) was at least as potent as the clinically used positive controls, sodium nitroprusside and glyceryl trinitrate, while the morpholine analogue (Example 3, FIG. 2) also had an $EC_{50}$ (concentration required to induce 50% relaxation) in the submicromolar range.

Pharmacology Experiment III

Each of the following compounds:

(a) bis (azetidine) bis (nitric oxide), adduct
(b) bis (azacyclooctane) bis (nitric oxide) adduct,
(c) bis (2-methylpiperidine) bis (nitric oxide) adduct,
(d) bis (3-methylpiperidine) bis (nitric oxide) adduct,
(e) bis (4-methylpiperidine) bis (nitric oxide) adduct,
(f) bis (2-ethylpiperidine) bis (nitric oxide) adduct,
(g) bis (4-phenylpiperidine) bis (nitric oxide) adduct,
(h) bis (2-propylpiperidine) bis (nitric oxide) adduct,
(i) bis (4-propylpiperidine) bis (nitric oxide) adduct,
(j) bis (4-tert.butylpiperidine) bis (nitric oxide) adduct,
(k) bis (2-methylpyrrolidine) bis (nitric oxide) adduct,
(l) bis (3-methylpyrrolidine) bis (nitric oxide) adduct,
(m) bis (1,2,3,6-tetrahydropyridine) bis (nitric oxide) adduct,
(n) bis (3-pyrroline) bis (nitric oxide) adduct,
(o) bis (hexamethyleneimine) bis (nitric oxide) adduct,
(p) bis (1-aza-12-crown-4) bis (nitric oxide) adduct,
(q) bis (1-aza-15-crown-5) bis (nitric oxide) adduct and
(r) bis (1-aza-18-crown-6) bis (nitric oxide) adduct, is tested for cardiovascular properties utilizing the procedures set forth in the above Experiments I and II; each of the compounds (a) to (r) is expected to possess cardiovascular properties in mammals, and to be useful in the present inventive methods and pharmaceutical compositions.

Pharmaceutical Compositions

The compositions of this invention are useful for treating any cardiovascular disorder that will respond favorably to a decrease in blood pressure. These disorders include chronic hypertension, hypertensive crisis (an acute hypertensive emergency), acute congestive heart failure, angina, acute myocardial infarction, left ventricular failure, cerebrovascular insufficiency and intracranial haemorrhage. Because of the fast response upon intravenous injection the compositions are particularly advantageous for treating acute disorders such as hypertensive crisis, toxemia of pregnancy and acute congestive heart failure. The preferred method of administration is by injection into the blood system, most preferably by intravenous injection. The chronic disorders can be treated by continuous intravenous infusion. A suitable dosage for intravenous administration is about 0.01 to 10.0 mg/kg per day.

The pharmaceutical compositions of the invention are comprised of the compounds of Formula I and a pharmaceutical carrier. The carrier can be any of those conventionally used and is limited only by chemico-physical considerations such as solubility and lack of reactivity with the compound and by the route of administration. For intravenous administration, the carrier will be aqueous and may contain solubilizing agents, buffers, preservatives, antioxidants, chelating agents, and agents to control the tonicity, such as dextrose or sodium chloride. The requirements for effective pharmaceutical carriers for injectable compositions are well known by one of ordinary skill in this art. (See "Pharmaceutics and Pharmacy Practice", J. B. Lippincott Company, Philadelphia, 1982, edited by Banker and Chalmers, pages 238-250, which are incorporated by reference, also see ASHP "Handbook on Injectable Drugs" 4th edition by Trissel, pages 622-630, which lists commercially available intravenous infusion solutions, these pages are incorporated by reference.) The compounds may also be formulated as inclusion complexes, such as, for example, cyclodextrin inclusion complexes; or the compounds may be carried within liposomes. Preferred pharmaceutical carriers for injection are PBS (phosphate buffered saline), 5% dextrose and sterile water. Since the compounds of formula I are subject to being oxidized by oxygen, an antioxidant, such as ascorbate, can be added to the carrier to increase the shelf-life.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Each of the publications and patents referred herein above are expressly incorporated herein by reference in their entirety.

What is claimed is:

1. An injectable pharmaceutical composition comprising an effective amount of a compound of the Formula:

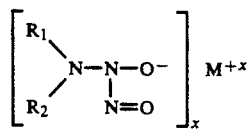

wherein $R_1$ and $R_2$ together with the nitrogen atom are bonded to form a heterocyclic group of the Formula

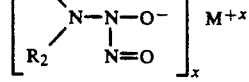

wherein Z is 1 to 5, $M^{+x}$ is a pharmaceutically acceptable cation, and x is the valence of the cation; and a pharmaceutically acceptable sterile carrier.

2. The composition of claim 1, wherein the Formula I compound is a bis(morpholino)bis (nitric oxide) adduct.

3. The composition of claim 1, wherein $M^{+x}$ is $Na^+$, $K^+$, $Ca^{+2}$ or $(R_1)(R_2)NH_2^+$.

4. The composition of claim 1, wherein $R_1$ and $R_2$ together with the nitrogen they are bonded to form a heterocyclic ring selected from the group consisting of: morpholino, 1-aza-12-crown-4, 1-aza-15-crown-5, and 1-aza-18-crown-6.

5. A method of treating a cardiovascular disorder in a mammal in need of such treatment, the method comprising lowering the blood pressure of the mammal by administering to the mammal a blood pressure lowering effective amount of a compound of the formula:

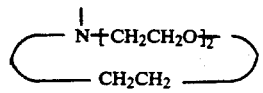

wherein $R_1$ and $R_2$ together with the nitrogen atom are bonded to form a heterocyclic ring of the formula

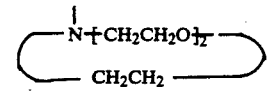

wherein Z is 1 to 5, $M^{+x}$ is a pharmaceutically acceptable cation, and x is the valence of the cation.

6. The method of claim 5, wherein the formula I compound is a bis(morpholino)bis (nitric oxide) adduct.

7. The method of claim 5, wherein the cardiovascular disorder treated is chronic hypertension, hypertensive crisis, acute congestive heart failure, angina, acute myocardial infarction, left ventricular failure, cerebrovascular insufficiency or intracranial hemorrhage.

8. The method of claim 5, wherein $R_1$ and $R_2$ together with the nitrogen they are bonded to form a heterocyclic ring selected from the group consisting of: morpholino, 1-aza-12-crown-4, 1-aza-15-crown-5, and 1-aza-18-crown-6.

* * * * *